United States Patent [19]

Hori et al.

[11] 4,208,265
[45] Jun. 17, 1980

[54] OXYGEN SENSOR ELEMENT AND PROCESS OF MANUFACTURE

[75] Inventors: Ryuzo Hori; Kiyoshi Uchida; Yasuhiro Otsuka; Shinichi Matsumoto; Hiroshi Wakisaka, all of Toyota, Japan

[73] Assignee: Toyota Jidosha Kogyo Kabushiki, Toyota, Japan

[21] Appl. No.: 900,858

[22] Filed: Apr. 28, 1978

[30] Foreign Application Priority Data

Nov. 11, 1977 [JP] Japan .................. 52-135330

[51] Int. Cl.$^2$ ............................................ G01N 27/58
[52] U.S. Cl. ............................ 204/195 S; 29/592 R; 427/123
[58] Field of Search .............. 204/1 S, 195 S; 29/592; 427/123

[56] References Cited

U.S. PATENT DOCUMENTS

| 3,468,780 | 9/1969 | Fischer | 204/195 S |
| 3,576,730 | 4/1971 | Spacil | 204/195 S |
| 3,578,578 | 5/1971 | von Krusenstierna | 204/195 S |
| 3,752,753 | 8/1973 | Fitterer | 204/195 S |
| 3,767,469 | 10/1973 | Flais et al. | 204/195 S |
| 3,841,987 | 10/1974 | Friese et al. | 204/195 X |
| 4,021,326 | 5/1977 | Pollner et al. | 204/195 S |
| 4,040,929 | 8/1977 | Bauer | 204/195 S |
| 4,080,276 | 3/1978 | Bode | 204/195 S |

Primary Examiner—G. L. Kaplan
Attorney, Agent, or Firm—Brisebois & Kruger

[57] ABSTRACT

An oxygen sensor element is manufactured by successively forming on the outside of the output lead wire, a solid pole, a first metal electrode layer, a solid electrolyte layer, and a second metal electrode layer from inside to outside.

19 Claims, 6 Drawing Figures

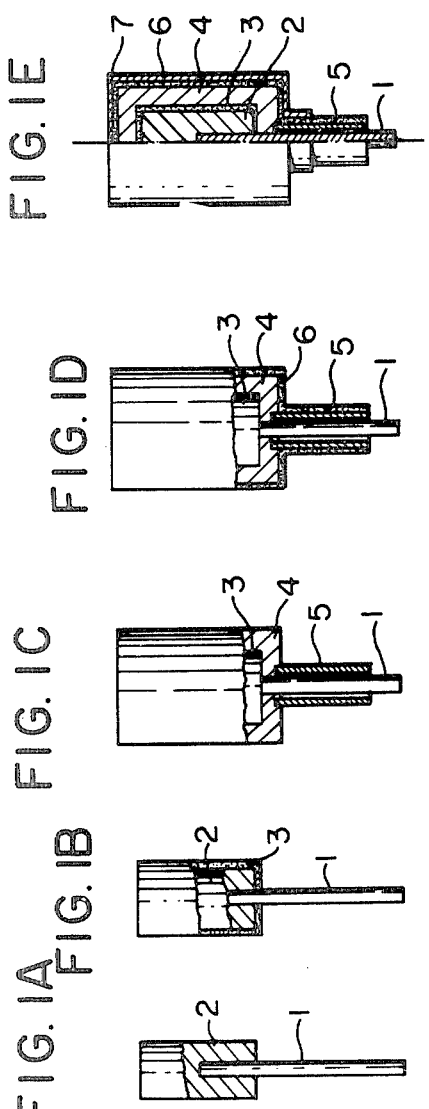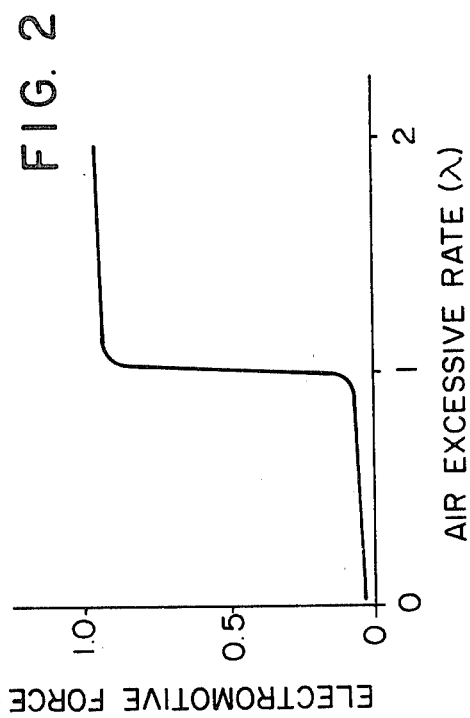

OXYGEN SENSOR ELEMENT AND PROCESS OF MANUFACTURE

BACKGROUND OF THE INVENTION (1) Field of the Invention

The present invention relates to an oxygen sensor element and its manufacturing process. More specifically, the invention relates to the manufacture of an oxygen sensor and an oxygen sensor element which is used as a unit for detection of oxygen concentration in the oxygen sensor to determine the concentration of oxygen in exhaust gas in an emission control system for disposing of the three harmful components of auto engine emissions, i.e., unburnt hydrocarbons, carbon monoxide and nitrogen oxides, simultaneously through reaction with a catalyst ("three-way system").

(2) Description of the Prior Art

Generally an oxygen sensor is equipped with an oxygen sensor element which is an oxygen concentration cell consisting of a solid electrolyte of a specific ceramic material with oxygen ion conductivity, in which the oxygen concentration on the measured gas side is determined by measuring the electromotive force produced through a difference in the oxygen partial pressure between the measured gas side and the reference gas side.

In the conventional process of manufacturing the oxygen sensor element, a solid electrolyte vessel with one end open is prepared; on the inside and outside surfaces of this vessel a porous metal electrode layer is formed; a metal or a mixture of a metal and its oxide as the reference oxygen partial pressure-generating substance is charged into the vessel and sintered; a lead wire is put through the opening of the vessel and into contact with the metal electrode layer on the inside surface of the solid electrolyte vessel; and then the opening of the solid electrolyte vessel is sealed, with the lead wire running through the seal.

In such a process, however, molding or otherwise forming the solid electrolyte in the form of a vessel is complicated and hinders mass production of the oxygen sensor element. In addition, the formation of the required metal electrode layer on the inside surface of the solid electrolyte vessel is difficult to control, and hence uniform quality oxygen sensor elements are difficult to make. Moreover, because the solid electrolyte vessel is formed, and then filled with a metal or a mixture of a metal and its oxide which are then sintered, heat and stress are developed in the solid electrolyte vessel and the metal electrode layer resulting in changes of the electrical, mechanical and thermal properties, and causing further variations in quality of the oxygen sensor elements. Furthermore, the liability to such troubles leads to a great bother in the control of the manufacturing steps.

Meanwhile, because of the necessity to keep the reference oxygen partial pressure of the sintered metal (or a sintered mixture of a metal and its oxide) at a constant level, the opening of the solid electrolyte vessel must be sealed and accordingly, a special seal is needed to assure perfect airtightness. This is another problem area which complicates the manufacture of the oxygen sensor element and renders it impossible to make the oxygen sensor element itself compact.

SUMMARY OF THE INVENTION

The object of the present invention is to provide a process for making an oxygen sensor element which facilitates the formation of the solid electrolyte layer, by changing the sequence of the manufacturing steps of the oxygen sensor element to eliminate the necessity of preliminarily forming the solid electrolyte vessel, and thereby increasing the mass productivity of the oxygen sensor element.

Another object of the present invention is to provide a process for manufacturing an oxygen sensor element characterized by ease of control of the manufacturing steps.

Still another object of the present invention is to provide a process for manufacturing an oxygen sensor element which facilitates the control of the formation of a metal electrode layer, particularly the layer which is on the inside surface of the solid electrolyte vessel, by changing from the known sequence of steps of manufacture of an oxygen sensor.

Still another object of the present invention is to provide a process for manufacturing an oxygen sensor element, in which the sequence of manufacture of the oxygen sensor element is changed such that there is no change in the electrical, mechanical and thermal properties of the solid electrolyte in the course of the forming of the element, there is no fear of reduction of or variance in product quality of the oxygen sensor element.

Still another object of the present invention is to provide a process for the manufacture of an oxygen sensor element which simplifies sealing the solid pole (reference oxygen partial pressure-generating substance) which consists of a metal or a mixture of a metal and its oxide.

Still another object of the present invention is to provide a process for manufacturing a compact oxygen sensor element.

Still another object of the present invention is to provide a process for manufacturing an oxygen sensor element with enhanced electrical insulation between the first metal electrode layer and the second metal electrode layer.

Still another object of the present invention is a process for manufacturing an oxygen sensor element with increased protection of the outer most surface layer.

Additional objects of the present invention will become apparent from the following detailed account of the invention and the attached drawings.

BRIEF DESCRIPTION OF THE DRAWINGS

FIG. 1 illustrates one embodiment of the present invention, (A) (B) (C) (D) and (E) being respectively partially cutaway elevation views showing the internal structure of an oxygen sensor element at successive stages of manufacture, according to the invention; and FIG. 2 is a graph illustrating the electromotive force response characteristics of the oxygen sensor element produced according to the present invention.

DESCRIPTION OF PREFERRED EMBODIMENT

There are four steps in the manufacturing process of an oxygen sensor element according to the present invention.

In the first step illustrated in FIG. 1(A), an output lead wire 1 is prepared and at one end of this wire a solid pole 2, for generation of the reference oxygen partial pressure and which consists of a metal or a mixture of a metal and its oxide, is formed by sintering. As the material for the output lead wire 1, a metal wire characterized by resistance to oxidation and heat, and having a coefficient of thermal expansion approximate to that of the solid electrolyte layer is preferable; for instance, for the wire, either Pt or Pt-Rh is available. As a metal or a mixture of a metal and its oxide for the solid pole 2, any one selected from among Ni, Ni.NiO; Cu, Cu.CuO; Fe, Fe.FeO is available. For prevention of over-sintering, blending of $\alpha$-$Al_2O_3$ as an anti-over sinter agent in the material of solid pole 2 before sintering is desirable. The solid pole 2 can be formed on the end of wire 1 by molding particles or powder, directly on the end of the wire in the shape of a cylinder.

In the second step illustrated in FIG. 1(B), the first metal electrode layer 3 (which ultimately becomes the internal electrode) is formed on the entire outside surface of the solid pole 2, so that a part of layer 3 contacts the lead wire 1. As the material for layer 3, a substance with high resistance to oxidation and high catalytic activity, for instance Pt alone or a mixture of Pt and at least one material selected from among Pd, Rh, or Ag is available. For the practical purpose of forming layer 3 on the outside surface of the solid pole 2, any one of the following processes can be adopted: a process of decomposing these metals by means of salts; a process of coating and baking platinum paste etc.; a chemical or electrical plating process; an ion-plating process. In whatever process, the electrode layer 3 has only to be formed on the outside surface of the solid pole 2. Therefore the formation of layer 3 is extremely easy to control and a variance in the layer thickness is less likely to happen. Since in this step the metal electrode layer 3 is formed on the surface of a sintered pole, the electrode layer formed can itself be gas-permeable.

In the third step illustrated in FIG. 1(C), a solid electrolyte layer 4 is formed on the entire outside surface of the first metal electrode layer 3. Without preparing a solid electrolyte vessel in advance as done conventionally, the solid electrolyte layer 4 is formed directly on the outside surface of the first metal electrode layer 3, thereby dispensing with any apparatus for vessel formation and simplifying the step of forming the solid electrolyte layer. The solid electrolyte layer 4 is formed desirably in such a manner that an insulating tube 5 is attached to the exposed portion of the output lead wire 1 and the tube 5 is partially embedded in the electrolyte layer 4. Instead of attaching the insulating tube 5, it is possible to form a coating of insulating material on the wire by metallizing.

The solid electrolyte 4 may consist of anything which is oxygen ion-conductive; $ZrO_2$ (zirconia), $HfO_2$ or $CeO_2$ stabilized with, for instance, CaO (calcia), MgO (magnesia) or $Y_2O_3$ (yttria) is available. As a practical method of formation of the electrolyte layer 4, a metallizing process, a sintering process or a hotpress process can be used. As the material for the insulation tube 5 or for insulation coating, anything which is resistant to oxidation and heat and has a thermal expansion coefficient close to that of the solid electrolyte layer 4 is available; for instance, stabilized $ZrO_2$ (zirconia), $Al_2O_3$ (alumina) or $MgO.Al_2O_3$ (spinel).

In the fourth step illustrated in FIG. 1(D), the second metal electrode layer 6 (external electrode) is formed on the outside surface of the solid electrolyte layer 4. The material available for the layer 6 is the same as the one for the first metal electrode layer 3 and the practical methods available for formation of layer 6 are the same as those for formation of layer 3. Since the solid electrolyte layer 4 has a rough surface, the second metal electrode layer 6 formed on that surface will be porous with gas permeability.

If the electrode layer 6 is formed as an extension around the insulation tube 5, as shown at FIG. 1(D), electric connection to the fitting means (not shown) will be easy.

In the present embodiment, a fifth step illustrated in FIG. 1(E) is involved, in which a protective porous coat 7 for the second metal electrode layer 6 is additionally formed on the outside surface of layer 6. The protective coat 7 can be formed only when it is necessary. As the material for coat 7, the same material as used for the insulation tube 5 is available and the coat 7 can be provided by the same process as described for the insulation tube 5. If the porous coat 7 is provided as a partial extension of the surface of the second metal electrode layer 6 around the insulation tube 5, the base of the insulation tube 5 will be mechanically more strengthened.

A specific example of the process according to the present invention will now be described in detail.

EXAMPLE

A mixture of carbonyl decomposed iron powder ($\alpha$-Fe) 95 mole % and iron monoxide (FeO) 5 mole % was adopted as the material for the solid pole 2 and to this mixture was added 30% by weight of $\alpha$-$Al_2O_3$ as the anti-over sinter agent. Using the powder blend thus obtained, a piece measuring about 1.5 mm thick and about 4 mm in diameter was molded, with a Pt wire of 0.3 mm diameter buried therein as the output lead wire 1. This piece was heated at 1,300° C. for 30 minutes in an Ar gas stream, thereby yielding a sintered solid pole 2.

The surface of the sintered product 2 was ion-plated with Pt to form the first metal electrode layer 3 under the following conditions: furnace Ar gas pressure $1 \times 10^{-2}$ torr; discharge voltage 4 Kv; Pt vapour deposition rate 30 Å/min; deposition time 1 hr; gap between vapour source and product about 25 cm; and Pt-melting electron beam output 5 Kw.

The sintered product 2 with the first metal electrode layer 3 formed thereon was plasma-sprayed with zirconia to form a solid electrolyte layer 4 on the surface of said electrode layer 3, (with formation of the insulation tube 5 omitted), under the following conditions: material powder-Meteco-made plasma-spraying powder No. 202 ($ZrO_2$—20 mold % $Y_2O_3$); plasma arc current—500 A; arc voltage—65 V; gases used and their flow rates—$N_2$, 100 SCFH (Standard Cubic Feet per Hour) and $H_2$, 15 SCFH; powder feed rate—70 g/min; distance between plasma gun and metallized object—80~100 mm; one plasma-spraying pass—10~15 seconds; number of passes—5~6; and plasma-spraying thickness—0.4~0.8 mm.

On the outside surface of the stabilized zirconia solid electrolyte layer 4, the second metal electrode layer 6 was formed in the same way as layer 3 was formed. Further, using Meteco-made plasma-spraying powder No. 105 SF (alumina) and a plasma arc current 300 A under the same plasma-spraying conditions as adopted for the first metal electrode layer 3, a porous coat 7 of about 50$\mu$ thickness was plasma-sprayed to complete an oxygen sensor element.

The results of testing the performance of the oxygen sensor element thus manufactured are summarized in FIG. 2. In the test of electromotive force vs. excess air rate ($\lambda$), the oxygen sensor was held at 500° C.; a mixture of 1 vol % $H_2$ + 99 vol % $N_2$ was introduced to the measured gas side at a rate of 2000 cc/min; with addition of air, the excess air rate ($\lambda$) was varied in the rate of 0~2; and thereby the electromotive force generated by the oxygen sensor element was measured by a voltmeter of input impedance 1000 MΩ.

As seen from FIG. 2, the oxygen sensor element according to the present invention shows a steep rise of the electromotive force in the vicinity of the excess air rate $\lambda$ = 1 and generates a potential close to the theoretical electromotive force, thus exhibiting an excellent performance as the element to be used in a "three-way system".

As described above, in the process according to the present invention the first metal electrode layer, the solid electrolyte layer and the second metal electrode layer are successively formed on the outside of the solid pole for generation of the reference oxygen partial pressure; therefore the necessity to prepare a solid electrolyte vessel in advance is obviated; the number of work steps can be reduced; and the mass productivity can be enhanced. Since the first metal electrode layer (internal electrode) is formed on the outside surface of the solid pole 2 (rather than on the inside surface of an electrolyte vessel, as in the prior art), the layer formation is easy to control and thus variations in the layer thickness can be prevented.

Moreover, since the solid electrolyte layer is formed on the outside surface of the solid pole which has been previously sintered, there is no heating or pressurizing after layer formation which could cause a change in the electrical, mechanical and/or thermal properties; therefore the product quality of the oxygen sensor element can be increased with little variance; and accordingly the control of the work steps is easy.

Furthermore, since the solid pole is enveloped with a solid electrolyte layer, a perfect airtight seal can be attained without any special means and thus the oxygen sensor element can be quite compact.

Furthermore, the oxygen sensor element, in the form of an integrated structure, according to the present invention, possesses an excellent resistance to thermal shock.

This application is related to application in Japan No. Sho 52-135330, filed Nov. 11, 1977 and its disclosure is incorporated into this application by reference.

What is claimed is:

1. Process for manufacturing an oxygen sensor element comprising the steps of:
   (a) forming a sinterable mass of an oxygen reference material around an output lead wire, the sinterable mass being of a material selected from the group consisting of a metal, or a mixture of a metal and its oxide, said sinterable mass containing an anti-over sintering agent;
   (b) sintering said mass of reference material to form a porous sintered mass of oxygen partial pressure generating material in the form of a solid pole with the lead wire embedded in the material;
   (c) then coating a first metal layer onto the outside surface of the solid pole so that the first metal layer electrically contacts the lead wire;
   (d) then coating the entire external surface of the first metal layer coated solid pole with a solid electrolyte; and
   (e) then coating a second metal electrode layer on the outside surface of the solid electrolyte layer.

2. A method according to claim 1 wherein said oxygen reference material consists essentially of a mixture of a metal and its oxide.

3. Process of claim 1, wherein said step of sintering comprises, sintering the solid pole on an output lead wire of a material selected from the group consisting of Pt or Pt-Rh.

4. Process of claim 1, wherein said step of sintering comprises, sintering a solid pole from a material selected from among Ni, Ni/NiO, Cu, Cu/CuO, Fe, and Fe/FeO.

5. Process of claim 4, wherein $\alpha$-$Al_2O_3$ is added to the material of said solid pole before sintering as anti-over sinter agent.

6. Process of claim 1, wherein said step of forming a solid electrolyte layer comprises forming the solid electrolyte layer from a material selected from among $ZrO_2$ (zirconia), $HfO_2$, and $CeO_2$, which have been stabilized with a material selected from among CaO, MgO and $Y_2O_3$.

7. Process of claim 1, wherein said first metal electrode layer and second metal electrode layer are constituted of either Pt alone or Pt containing at least one material selected from among Pd, Rh and Ag.

8. Process of claim 1, wherein said output lead wire is embedded in said lead wire prior to sintering.

9. Process of claim 1, wherein said first metal electrode layer is formed on the outside surface of said solid pole by a process selected from among: decomposition by metal salt, baking of platinum paste, chemical or electrical plating, and ion plating.

10. Process of claim 1, wherein said solid electrolyte layer is formed on the outside surface of said first metal electrode layer by a process selected from among: plasma-spraying, sintering, and hot pressing.

11. Process of claim 1, further comprising embedding an insulation tube in said solid electrolyte layer to partially cover an exposed portion of said output lead wire.

12. Process of claim 11, wherein said second metal electrode layer is formed on the outside surface of said solid electrolyte layer and on the outside surface of said insulation tube.

13. Process of claim 1, further comprising insulating an exposed portion of the wire by forming on the wire an insulation tube from a material selected from among $ZrO_2$ (zirconia), $Al_2O_3$ (alumina) and $MgO.Al_2O_3$ spinel.

14. Process of claim 1, wherein said step of forming a second metal electrode layer on the outside surface of said solid electrolyte comprises forming said electrode layer by a process selected from among: plasma-spraying, sintering and hot pressing.

15. Process of claim 1, further comprising forming a porous coating on the outside surface of said second metal electrode layer.

16. Manufacturing process of claim 15, wherein said porous coating is formed from a material selected from among stabilized $ZrO_2$, $Al_2O_3$ and $MgO.Al_2O_3$.

17. Manufacturing process of claim 15, comprising forming said porous coating by a process of plasma-spraying.

18. An oxygen sensor element comprising:
   an output lead wire,
   a porous sintered mass of oxygen partial pressure generating material in the form of a solid pole formed onto one end of said output lead wire,
   a first metal electrode layer formed on the outer surface of said solid pole so that the first metal electrode layer electrically contacts said output lead wire, a solid electrolyte layer formed wholly around the outer surface of said first metal electrode layer and solid pole, and a second electrode layer formed on the outer surface of said solid electrolyte layer and electrically insulated from said output lead wire.

19. The oxygen sensor element claimed in claim 18, further comprising a protective porous coat on the outer surface of said second electrode layer.

* * * * *